US006187327B1

(12) United States Patent
Stack

(10) Patent No.: US 6,187,327 B1
(45) Date of Patent: Feb. 13, 2001

(54) ANTIMICROBIAL SANITIZING LOTION WITH SKIN PROTECTION PROPERTIES

(76) Inventor: Kevin Stack, 6301 Collins Ave., Unit 1704, Miami Beach, FL (US) 33141

( * ) Notice: Under 35 U.S.C. 154(b), the term of this patent shall be extended for 0 days.

(21) Appl. No.: 09/314,553

(22) Filed: May 19, 1999

(51) Int. Cl.$^7$ .................................................. A01N 25/00
(52) U.S. Cl. .......................... 424/405; 424/400; 424/404; 424/401
(58) Field of Search ................................... 424/405, 484, 424/400, 401, 404; 514/873

(56) References Cited

U.S. PATENT DOCUMENTS

| 5,173,216 | 12/1992 | Uhlig . |
|---|---|---|
| 5,259,984 | 11/1993 | Hull . |
| 5,540,853 | * 7/1996 | Trinh et al. ........................... 510/101 |
| 5,562,912 | 10/1996 | Burke et al. . |
| 5,591,442 | 1/1997 | Diehl et al. . |
| 5,629,006 | 5/1997 | Hoang et al. . |
| 5,650,143 | 7/1997 | Bergmann et al. . |
| 5,719,113 | 2/1998 | Fendler et al. . |
| 5,728,662 | 3/1998 | Vlasblom . |
| 5,750,579 | 5/1998 | Kamishita et al. . |
| 5,767,163 | 6/1998 | Kundsin . |
| 5,772,640 | 6/1998 | Modak et al. . |

* cited by examiner

*Primary Examiner*—D. L. Jones
(74) *Attorney, Agent, or Firm*—McHale & Slavin

(57) ABSTRACT

The present invention is directed toward an antimicrobial hand sanitizing lotion in the form of a medicated polymer/emulsion based product and the method by which it is produced. The product is intended to be used as a topical antimicrobial and skin protective lotion and contains 2,4,4'-trichloro-2'-hydroxydiphenyl ether as the antimicrobial agent of choice in a base which forms a hydrophobic protective barrier, having persistent antimicrobial properties, upon application to the skin.

3 Claims, No Drawings

ANTIMICROBIAL SANITIZING LOTION WITH SKIN PROTECTION PROPERTIES

FIELD OF THE INVENTION

This invention relates to sanitizing lotions having antimicrobial properties; and particularly to a highly persistent antimicrobial hand sanitizing lotion which displays unique barrier properties.

BACKGROUND OF THE INVENTION

Hand washing has long been recognized as a particularly effective method for reducing the transmission of communicable diseases. In hospitals, where patients are in a weakened condition, it is most important for health-care professionals to utilize an antimicrobial hand cleaning composition to prevent the spread of various pathogenic microorganisms. Furthermore, it is necessary to treat parts of the skin and mucous membranes antiseptically prior to any type of surgical procedure, injection, or puncture so as to prevent the transmission of infectious microorganisms. In such environments, compositions such as alcohols are effective antimicrobials. However, the defatting properties of alcohols cause chapping and cracking to occur to the skin of the user. The resultant damaged skin is then more prone to additional infectious contamination, since pathogenic microorganisms can enter and evade sanitizing materials by residing within the cracked epidermal layer. Additionally, the presence of alcohols inhibits the foaming action of various detergent compositions which are likely to be used in combination therewith. Various antimicrobials are known for use in such formulations, for example, iodophors, iodine formulations, phenolic compounds, e.g. hexachlorophene, and bisbiguanides, e.g. chlorhexidene gluconate. Such antimicrobial ingredients are also well-known additives for a variety of products, such as deodorant soap bars, underarm deodorants, liquid soaps and fabric treatments.

In order to form an efficacious antimicrobial product which is not injurious to the user's skin, various proposals have been made. Improvements in mildness and skin afterfeel have called for the addition of such additives as glycerin, sorbitol, vitamin E, coco fatty acid derivatives and their salts, alkyl quaternary salts and sugar esters.

DESCRIPTION OF THE PRIOR ART

U.S. Pat. No. 5,173,216 discloses a composition for decontaminating and/or disinfecting the hands comprising an amphoteric-cationic surfactant, a cationic surfactant, a wetting agent which is compatible with the cationic surfactant, and a nonionic regressing agent. The composition exhibits both bacteriostatic and fungistatic effectiveness at varying concentrations.

U.S. Pat. No. 5,719,113 discloses an antimicrobial cleansing composition containing chlorhexidine, a nonionic surfactant which does not include polyoxypropylene/polyoxyethylene block copolymers, an amphoteric surfactant, and an alkyl polyglucoside. Additionally included are viscosifiers or thickeners, emollients, fragrances, perfumes, coloring agents, preservatives, foaming agents, vitamins and fungicides.

U.S. Pat. No. 5,259,984 discloses a cleansing composition containing a storage-stable volatile polymer gel solution and a cleaning agent including an alkali metal hydroxide. In a preferred embodiment, the polymer gel solution includes a hydroxypropylmethylcellulose polymer. The composition is formed by forming a pre-mixed cleaning agent and a pre-mixed volatile aqueous gel solution. These pre-mixed components are then intermixed to form the final cleaner composition.

U.S. Pat. No. 5,562,912 discloses a cleansing composition containing an EO/PO/EO tri-block nonionic copolymer surfactant in conjunction with a generic skin cleanser composition.

U.S. Pat. No. 5,629,006 discloses a cleansing composition containing an alcohol, a block copolymer, a foaming surfactant, an emulsifier, a cleaning agent, a polyalkylene glycol, an emollient and water. Stepwise addition of the components with continuous mixing to a point of homogeneity is utilized in the method of formulation.

U.S. Pat. No. 5,728,662 discloses a cleansing composition which consists essentially of a d-limonene, a solvent, a $C_{11}$ alcohol ethoxylate, polyoxyethylene (20) sorbitan monooleate, a water-soluble acrylic polymer, sodium hydroxide, mixed isothioazolinones, 2,6-di-tert--butyl-p-cresol and water.

U.S. Pat. No. 5,767,163 discloses a cleansing composition and method for its use as a hand antiseptic. The composition is an alcoholic solution containing cetyl alcohol, glycolic acid, benzalkonium chloride and isopropyl alcohol as its major constituent.

U.S. Pat. No. 5,750,579 is drawn to a cleansing composition which is useful for the hands and fingers. The composition is in the form of a solution which comprises a disinfecting medicament in an alcohol and a thickening agent consisting of a combination of a carboxyvinyl polymer and a water-soluble, high molecular weight cellulose compound. The process of manufacture requires that various of the ingredients are blended to a point of homogeneity, resulting in a final, homogeneous composition.

U.S. Pat. No. 5,591,442 is drawn to an antiseptic and disinfectant hand cleaning composition containing a synergistic mixture of an alkyl alcohol component and a glycerol monoalkyl ether.

U.S. Pat. No. 5,650,143 drawn to a deodorant cosmetic stick composition provides a deodorant cosmetic stick product which has a translucent or transparent light transmitting appearance. The cosmetic stick contains propylene glycol, sodium stearate, dimethicone copolyol, TRICLOSAN, PENTADOXYNOL-200, and water.

U.S. Pat. No. 5772640 drawn to TRICLOSAN-containing medical devices, discloses polymeric medical articles containing the antiinfective agents chlorhexidine and TRICLOSAN. The patent discloses a synergistic relationship between these compounds which permits the use of relatively low levels of both agents, while achieving effective antimicrobial activity when these compounds are contained in either hydrophilic or hydrophobic polymers.

The prior art formulations suffer from the fact that increased use of various surfactants and lipid-restoring compositions reduce the effectiveness of the antimicrobial active ingredient. Therefore, if a composition including skin barrier properties and persistent anti-microbial characteristics could be formulated in such a way that both enhanced skin-care and increased antimicrobial effectiveness resulted, a long-felt need in the art would be satisfied.

SUMMARY OF THE INVENTION

The present invention describes an antimicrobial hand sanitizing lotion in the form of a medicated polymer/emulsion based product and the method by which it is produced. The product is intended to be used as a topical antimicrobial lotion. 2,4,4'-trichloro-2'-hydroxydiphenyl ether, available under the tradename TRICLOSAN or IRGASAN DP 300 from the Ciba Geigy Corp., is the antimicrobial agent of choice in the present formulation. TRICLOSAN has demonstrated efficacy against the following gram-positive and gram-negative bacteria, plus fungi and yeasts:

GRAM-POSITIVE BACTERIA

Bacillus subtilis
Bacillus megatherium
Bacillus cereus
Bacillus cereus var. mycoides
Clostridium botulinum
Clostridium tetani
corynebacterium diphtheriae
Corynebacterium acnes*
Diplococcus pneumonise
Lactobacillus arabinosus
Lactobacillus fermenti
Mycobacterium tuberculosis
Mycobacterium smegmatis
Mycobacterium phlei
Sarcina lutea
Sarcina ureae
staphylococcus aureas
Staphylococcus albus
streptococcus agalactiae
streptococcus haemolyticus A
streptococcus faecalis
streptococcus pyogenes
*Propionibacterium acnes

GRAM-NEGATIVE BACTERIA

Aerobacter aerogenes
Alraligenes; faecalis
Brucella intermedia
Brucella abortus
Brucella melitensis
Brucella suis
cloaca cloacae
Escherichia coli
Haemophilus Influenzae
Klebsiella edwardsii
Klebsiella aerogenes
Klebsiella pneumoniae
Loeffierella mallei
Loeffierella pseudomallei
Moraxells duplex
Moraxella glucidolytica
Moraxella lwoffi
Neisseria catarrhilis
Pasteurella septica
Pasteurella pseuclotuberculosis
Proteus vulgaris
proteus mirabills
Pseudomonas aeruginosa
Pseudomonas fluorescens
Salmonella enteritidis
Salmonella typhimurium
salmonella typhi
Salmonella paratyphi A
salmonella paratyphi B
Salmonella pullorum
Serratia marcescens
Shigella flexneri
Shigella sonnei
Shigelle dysenteriae
Vibrio cholerae
Vibrio eltor

FUNGI AND YEASTS

Aspergillus niger
Aspergillus furnigatus
Candida albicans
Epidermophyton floccosum
Keratinomyces ajelloi -continued Tochophylon mentagrophytes
Trichophylon rubrum
Trichophyton tonsurans It has been discovered that incorporation of TRICLOSAN in a topical lotion comprised of a Surfactant Phase, and a Wax Phase results in a product which is particularly effective in preventing cross-contamination of pathogenic microorganisms in the workplace. The product is persistent in that it significantly reduces the incidence of bacteria on skin surfaces for a period of about 3–4 hours. It is applicable to any area of intact skin, and will kill pathogenic bacteria on contact and remain effective for extended periods of time. The specially formulated antiseptic handwash of the invention is a non-toxic and hypoallergenic lotion containing a broad spectrum antimicrobial which forms a polymeric film on healthy skin. It is a completely safe and long lasting product which will not rub off on food or the like due to its unique bonding agent. The hydrophobic portion of the process utilizes a USP White Wax in combination with the acrylic carbomer. The wax in solution in co-ordination with the product backbone (CARBOPOL 934-P), melts through the heat of the hand. The wax phase spreads over the skin with the CARBOPOL theorized to act in two ways. The acrylate chains are theorized to intercalate into the wax matrix and stabilize the wax by adding support to the horizontal spreading and layering of the wax. Further, the CARBOPOL is theorized to interact with the skin surface relative to the horizontal wax layer. The combination of these interactions forms a physical hydrophobic layer which resides on the skin surface and provides a barrier which would inhibit penetration of liquids which are primarily hydrophilic in nature. The wax is solubilized and dispersed with the aid of surfactants and dimethicone within an alcohol/glycerol base. Stearic acid, particularly triple pressed, is noted as being critical to affecting complete solubilization of the raw materials in the wax phase. At appropriate concentration ranges of the antimicrobial ingredient, the product is efficacious for use by healthcare professionals in that it is a highly effective, broad spectrum bactericidal composition.

One of the unique properties of the product is its ability to protect the skin from relatively strong acids and bases. Tests conducted on metallic surfaces demonstrated enhanced longevity of the metallic substrates when exposed to corrosive environments. The barrier properties of the instant composition further increase the efficiency of bacterial removal from the skin's surface. The product is further characterized by exhibiting a highly persistent antimicrobial action. This persistence may be attributed to the stability of the wax/carbomer hydrophobic layer which allows for a unique physical presentation of the antimicrobial, e.g. TRICLOSAN, molecule. The stabilized barrier composition is stabilized by the CARBOPOL chains orientated into the wax phase. TRICLOSAN, being a hydrophobic molecule, would orientate with respect to the barrier layer, resulting in a product which maintains persistent skin contact and antimicrobial action. In combination, these properties result in a product having enhanced effectiveness in the removal of surface bacteria compared to washing with soap and water. This effectiveness persists for the duration of the presence of the product formulation on the skin. Application of this product prior to a soap and water hand washing has been clinically proven to enhance hand washing with a statistically significant increase in the removal of harmful bacteria from the skin surface, compared to ordinary hand washing without prior application of the product.

When used in combination with latex gloves, the product inhibits the growth of microorganisms underneath the latex gloves, protects hands from contamination should the gloves become damaged, moisturizes and soothes the skin to combat the potential damaging effects of latex, harsh soaps and frequent washing.

When processing the lotion of the present invention, the surfactant and wax phases are each formulated according to particular concentration and processing parameters, and then blended to form a Final Phase, resulting in a unique topical antimicrobial sanitizing and skin care product.

Accordingly, it is an objective of the instant invention to teach an antimicrobial sanitizing lotion, especially effective as a hand sanitizer, which is efficacious for a broad range of microorganisms and is characterized by unique skin protective barrier properties and enhanced persistence.

It is a further objective of the instant invention to teach a method for producing a sanitizing lotion wherein adherence to particular process parameters results in a unique final product.

It is yet another objective of the instant invention to teach a skin protective and sanitizing lotion wherein contact with the skin results in destruction of microbial contaminants and simultaneous formation of a hydrophobic skin protective surface layer.

It is a still further objective of the invention teach a skin protective and sanitizing lotion that enhances the capabilities of soaps and related skin-cleansers.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Production of the antimicrobial sanitizing lotion of the present invention relies upon strict adherence to a particular set of process parameters in order to arrive at a unique final product. In carrying out the process, particular attention must be given to the order of addition of the various components. Additionally, it is necessary that rigorous homogenization be carried out to form a "grain" free product. Finally, the various steps must be carried out within particular temperature ranges which are critical to the outcome of the process.

The product contains, as its active ingredient, TRICLOSAN (a Class III topical antimicrobial active ingredient. The finished product strength for TRICLOSAN ranges from (all percentages are percent by weight) 0.10%–0.35%, with a particularly preferred range being 0.117%–0.143% for general and food service usage and 0.27%–0.33% for the health care environment. The product is a viscous, flowing liquid polymer emulsion which is opaque and white in color, having a mild characteristic odor. The specific gravity of the product ranges from 0.960–0.980 at 25° C. and the pH of a 10% by volume aqueous solution is within the range of 6.5–7.1.

The excipients which are useful in forming the antimicrobial and skin protective lotion of the present invention are deionized water, in a range of 75–85 wt. %, VERSENE-100, in a range of 0.136–0.184 wt. %, CARBOPOL 934-P in a range of 0.245–0.455 wt. %, TRITON X-100 in a range of 2.55–3.45 wt. %, Propylene Glycol U.S.P. in a range of 0.85–1.15 wt. %, TERGITOL NP-9 in a range of 1.7–2.3 wt. %, DOWCIDE-A, in a range of 0.10–0.50 wt. %, Triethanolamine 85 % n.f, in a range of 0.85–1.15 wt. %, Chlorhexidine Digluconate 20 %, in a range of 0.16–0.75 wt. %, Alpha Tocopherol (Vitamin E U.S.P.), in a range of 0.09–0.11 wt. %, Stearic Acid—triple pressed in a range of 2.55–3.45 wt. %, Cetyl Alcohol n.f., in a range of 1.35–1.65 wt. %, Ethylene Glycol Monostearate, in a range of 0.675–0.825 wt. %, Dimethicone 1-45-350 cstks,in a range of 1.7–2.3 wt. %, U.S.P. White Wax in a range of 0.213–0.288 wt. %, and PARAGON MEPB in a range of 1.0–3.0 wt. %.

EXAMPLE 1

The following formulation was produced in accordance with the instant invention.

Excipients useful in the manufacture of this product were added in the following amounts:

| EXCIPIENT | % BY WEIGHT |
| --- | --- |
| (1) DEIONIZED WATER | 83.50 |
| (2) VERSENE-100 | 0.16 |
| (3) CARBOPOL 934-P | 0.35 |
| (4) TRITON X-100 | 3.00 |
| (5) PROPYLENE GLYCOL U.S.P. | 1.00 |
| (6) TERGITOL NP-9 | 2.00 |
| (7) DOWCIDE - A | 0.10 |
| (8) TRIETHANOLAMINE 85% N.F | 1.00 |
| (9) CHLORHEXIDINE DIGLUCONATE 20% | 0.16 |
| (10) ALPHA TOCOPHEROL (VITAMIN E USP) | 0.10 |
| (11) STEARIC ACID - TRIPLE PRESSED | 3.00 |
| (12) CETYL ALCOHOL N.F. | 1.50 |
| (13) ETHYLENE GLYCOL MONOSTEARATE | 0.75 |
| (14) DIMETHICONE L-45-350 CSTKS | 2.00 |
| (15) USP WHITE WAX | 0.25 |
| (16) PARAGON MEPB | 1.00 |

In formulating a 4,050 pound batch of the antimicrobial sanitizing and skin protective lotion of the invention, the following method steps were followed:

(A) A Surfactant Phase is formulated by combining the following ingredients:

1) Deionized Water of reagent grade exhibiting less than 1 microohm resistivity is first added to a mixing tank in an amount of 405.40 gallons (3,382.59 lbs.)

2) VERSENE 100 (or a like equivalent EDTA Sodium Salt)(6.06 lbs.) is added; followed by 3) CARBOPOL 934 P (or a like equivalent Acrylic Polymer) (14.18 lbs.)

The mixer is engaged in the reverse mode while the circulating pump is turned on to full open, yielding a flow rate of about 110–150 gpm at a pressure of about 60–110 psi, for recirculation of the mixture. Engagement of the pump in the reverse mode causes mixing to occur in a bottom to top direction within the tank. This reverse mode pumping coupled with the forceful agitation of the recirculating pump is critical in solubilizing the Carbopol 934 in the mixture.

Homogenization of the above-mentioned ingredients is then carried out for about 30–40 minutes utilizing a stator-bladed motor driven homogenizer under flow conditions of about 110–150 gpm and at a pressure of about 60–110 psi, which conditions are sufficiently rigorous to yield a "grain" free and highly uniform product.

The remaining raw materials:

4) TRITON X-100 Surfactant (or a like equivalent Octyl Phenyoxypolyethoxy non-ionic surfactant) 121.5 lbs 5) Propylene Glycol (USP) 40.50 lbs.

6) TERGITOL NP-9 Surfactant (or a like equivalent Nonylphenol polyethylene glycol ether non-ionic surfactant) 81.00 lbs.

7) DOWCIDE-A (or a like equivalent Sodium O-Phenylphenatetetrahydrate) 4.05 lbs.

8) IRGASAN DP300 (2,4,4'-trichloro-2'-hydroxydiphenyl ether)

| | |
|---|---|
| 4) TRITON X-100 Surfactant (or a like equivalent Octyl Phenyoxypolyethoxy non-ionic surfactant) | 121.5 lbs |
| 5) Propylene Glycol (USP) | 40.50 lbs. |
| 6) TERGITOL NP-9 Surfactant (or a like equivalent Nonylphenol polyethylene glycol ether non-ionic surfactant | 81.00 lbs. |
| 7) DOWCIDE-A (or a like equivalent Sodium O-Phenylphenatetetrahydrate) | 4.05 lbs. |
| 8) IRGASAN DP300 (2,4,4'-trichloro-2'-hydroxydiphenyl ether) | 5.25 lbs. |
| 9) Triethanolamine 85% N.F. | 40.50 lbs. |
| 10) Chlorhexidine Digluconate 20% | 6.06 lbs. |
| 11) Alpha Tocopherol | 4.05 lbs. | are weighed and added to the mixture.

It is noted that the hydrophilic portion of the product is modified by the use of the non-ionic surfactant (TRITON X-100) in a propylene glycol base. The hydrophilic phase is further modified due to the inclusion of TERGITOL NP-9 which includes the nonoxyl class of compounds.

Inclusion of Alpha Tocopherol (Alpha Tocopherol Acetate) commonly known as Vitamin E has a two-fold benefit. Its presence inhibits oxidation of the product as well as providing additional skin conditioning properties. Since tocopherols are freely soluble in alcohols and lipids, they easily penetrate the skin layer and provide conditioning benefits.

After all ingredients have been blended, the Surfactant Phase is then heated to within a range of about 70° C.–85° C., and maintained within this temperature range while mixing and pump recirculation are continued at about 110–150 gpm at a pressure of about 60–110 psi.

(B) The Wax Phase is next formulated by adding the following ingredients:

| | |
|---|---|
| Stearic Acid - Triple Pressed | 121.50 lbs. |
| Cetyl Alcohol N.F. | 60.75 lbs. |
| Ethylene Glycol Monostearate | 30.38 lbs. |
| Dimethicone L-45-350 cstks | 81.00 lbs. |
| White Wax (BARECO BE SQUARE) | 10.13 lbs.; | heating to within a range of about 70° C.–85° C., ideally about 77° C.–80° C.; and maintaining the temperature of the Wax Phase within this temperature range, while mixing at about 1500–1700 rpm using a direct drive mixer.

The use of a wax, e.g. BARECO BE SQUARE, or a like equivalent which is a USP grade White Wax having a melting point in the range of 70° C.–85° C., provides a unique property. The wax, which is in solution in coordination with the Carbopol-934-P, melts through contact with the heat of the hands. This in turn forms a physical hydrophobic layer and provides a barrier which appears to inhibit penetration of liquids which are primarily hydrophilic in nature. This property helps protect the user from injury due to contact injurious materials, e.g. with acids and/or bases. The wax is apparently solubilized and dispersed with the aid of the surfactants and Dimethicone within an alcohol/glycerol base. The presence of Stearic acid, particularly triple pressed, is critical to effecting the complete solubilization of the remaining Wax Phase materials. While not wishing to be bound to any particular theory, it is believed that the wax flattens to form a neutral and hydrophobic barrier. The carbomers are believed to support the wax layer in the horizontal plane and in attachment to the skin. The carbomer molecule, which is believed to physically intercalate within the wax phase, thereby reinforcing the wax layer, is also believed to interact with the skin thereby having a stabilizing effect upon the wax layer, which results in the enhanced persistence characteristic of the product. Lastly, it is believed that the processing steps orient the TRICLOSAN molecules to yield an optimum level of antimicrobial activity.

(C) The Final Phase is formed by adding the Wax Phase to the Surfactant Phase.

At the time of mixing, the Wax Phase is being maintained at approximately 85° C. and the surfactant Phase is maintained at 80° C. The mixing takes place by using homogenization, recirculation and pressure. Pressure generation is accomplished by restricting the outlet side of the pump, thus limiting the flow therethrough. This restriction keeps the pump stators full at all times, so as to avoid burn out of the pump. Such conditions are maintained for 45–60 minutes using a 20 HP pump, at a rate of about 100–150 gal/min, at about 60–110 psi, in reverse mode, restricting the outlet and recirculating the batch. After approximately 60 minutes, the temperature is then lowered to less than 50° C. so that the PARAGON MEPB Parabens materials can be safely added.

PARAGON MEPB (a mixture of Methyl, Ethyl, Propyl, and Butyl Parabenzene in a Phenoxy Ethanol solvent, or a like equivalent mixture) is then added (40.50 lbs.) and homogenization is continued for an additional 20–30 minutes with the recirculation pump on full open. In a particular embodiment, the MEPB mixture had about 16% methyl paraben, about 4% ethyl paraben, about 2% propyl paraben, about 6% butyl paraben and the remainder, about 72% of phenoxy-ethanol solvent.

It is theorized that inclusion of DOWCIDE-A, Chlorhexidine gluconate and the Parabens species in a Phenoxy-Ethanol solvent act as phenolic based preservatives to further increase hydrophobic solubility and thereby potentiate the active biocidal properties of the product.

It is further theorized that the propylene glycol, cetyl alcohol, phenoxyethyl alcohol, parabens, and octyl phenol act as permeability barriers to the bacterial lipid cell wall; that the TRITON-X 100 and triethanolamine offer an ionic approach to cell wall disruption via a chelation mechanism; and that the phenoxyethyl alcohol, parabens and DOWCIDE-A further provide cytoplasmic membrane permeation.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A method for forming a topical antimicrobial skin sanitizing and conditioning composition comprising:

1) forming a surfactant phase mixture, based upon a percentage by weight of the total composition, by first combining 83.5 wt. % deionized water, 0.16 wt. % EDTA Sodium Salt and 0.35 wt. % of an acrylic polymer within a vessel containing mixing means and recirculating means;

2) operating said mixing means in the reverse mode while operating the recirculation means at 100–150 gpm at a pressure of 60–110 psi, whereby the acrylic polymer is completely solubilized in said surfactant phase mixture;

3) homogenizing said surfactant phase mixture for 30–40 minutes under conditions sufficiently rigorous to yield a grain free, homogeneously blended mixture;

4) further adding, in the order and amounts stated, 3.0 wt. % Octyl Phenyoxypolyethoxy non-ionic surfactant, 1.0 wt. % Propylene Glycol (USP), 2.0 wt. % Nonylphenol polyethylene glycol ether non-ionic surfactant; 0.1 wt. % Sodium O-Phenylphenatetetrahydrate, 0.13 wt. % 2,4,4'-trichloro-2'-hydroxydiphenyl ether, 1.0 wt. % Triethanolamine 85% N.F., 0.16 wt. % Chlorhexidine Digluconate 20%, and 0.1 wt. % Alpha Tocopherol to said surfactant phase mixture;

5) further mixing the above ingredients to form a homogeneous blend while heating to within a temperature range of 70° C.–85° C.;

6) maintaining the surfactant phase mixture within said temperature range while mixing and pump recirculation are continued;

7) in a separate vessel, forming a wax phase mixture by combining 3.0 wt. % Stearic Acid, 1.5 wt. % Cetyl Alcohol N.F., 0.75 wt. % Ethylene Glycol Monostearate, 2.0 wt. % Dimethicone, and 0.25 wt. % USP White Wax;

8) heating said wax phase mixture to within a temperature range of 70° C.–85° C. and maintaining the temperature of said wax phase mixture within said temperature range while mixing;

9) adding the wax phase mixture to said surfactant phase mixture to form a final phase mixture under conditions of homogenization, recirculation and pressure for 45–60 minutes;

10) lowering the temperature of said final phase mixture to less than 50° C.; and 11) adding 1.0 wt. % of a mixture of Methyl,Ethyl,Propyl and Butyl Parabenzene in a Phenoxy-Ethanol solvent and continuing homogenization for an additional 20–30 minutes with total recirculation at a rate of about 100–150 gpm at a pressure of 60–110 psi.

2. The process of claim 1, wherein the wax phase in step (8) is maintained at a temperature of 77° C.–80° C.

3. A method for forming a topical antimicrobial skin sanitizing and conditioning composition comprising:

1) forming a surfactant phase mixture, based upon a percentage by weight of the total composition, by first combining 75–85 wt. % deionized water, 0.136–0.184 wt. % EDTA Sodium Salt and 0.245–0.455 wt. % of an acrylic polymer within a vessel containing mixing means and recirculating means;

2) operating said mixing means in the reverse mode while operating the recirculation means at 100–150 gpm at a pressure of 60–110 psi, whereby the acrylic polymer is completely solubilized in said surfactant phase mixture;

3) homogenizing said surfactant phase mixture for 30–40 minutes under conditions sufficiently rigorous to yield a grain free, homogeneously blended mixture;

4) further adding, in the order and within the range of amounts stated, 2.55–3.45 wt. % Octyl Phenyoxypolyethoxy non-ionic surfactant, 0.85–1.15 wt. % Propylene Glycol (USP), 1.70–2.30 wt. % Nonylphenol polyethylene glycol ether non-ionic surfactant; 0.1–0.5 wt. % Sodium O-Phenylphenatetetrahydrate, 0.10–0.35 wt. % 2,4,4'-trichloro-2'-hydroxydiphenyl ether, 0.85–1.15 wt. % Triethanolamine 85% N.F., 0.16–0.75 wt. % Chlorhexidine Digluconate 20%, and 0.09–0.11 wt. % Alpha Tocopherol to said surfactant phase mixture;

5) further mixing the above ingredients to form a homogeneous blend while heating to within a temperature range of 70° C.–85° C.;

6) maintaining the surfactant phase mixture within said temperature range while mixing and pump recirculation are continued;

7) in a separate vessel, forming a wax phase mixture by combining 2.55–3.45 wt. % Stearic Acid, 1.35–1.65 wt. % Cetyl Alcohol N.F., 0.675–0.825 wt. % Ethylene Glycol Monostearate, 1.7–2.3 wt. % Dimethicone, and 0.213–0.288 wt. % USP White Wax;

8) heating said wax phase mixture to within a temperature range of 70° C.–850° C. and maintaining the temperature of said wax phase mixture within said temperature range while mixing;

9) adding the wax phase mixture to said surfactant phase mixture to form a final phase mixture under conditions of homogenization, recirculation and pressure for 45–60 minutes;

10) lowering the temperature of said final phase mixture to less than 50° C.; and 11) adding 1.0–3.0 wt. % of a mixture of Methyl,Ethyl, Propyl and Butyl Parabenzene in a Phenoxy ethanol solvent and continuing homogenization for an additional 20–30 minutes with total recirculation at a rate of about 100–150gpm at a pressure of 60–110 psi.

* * * * *